United States Patent [19]
Courty et al.

[11] 4,277,369
[45] Jul. 7, 1981

[54] REGENERATION OF A CATALYST FOR AROMATIC HYDROCARBONS STEAM DEALKYLATION

[75] Inventors: Philippe Courty, Houilles; Jean Miquel, Paris; Germain Martino, Poissy; Alain Convers, Rueil Malmaison, all of France

[73] Assignee: Institut Francais du Petrole, Rueil-Malmaison, France

[21] Appl. No.: 98,453

[22] Filed: Nov. 29, 1979

[30] Foreign Application Priority Data

Nov. 29, 1978 [FR] France .................. 78 33910

[51] Int. Cl.$^3$ ............... B01J 21/20; B01J 23/96; C07C 4/18
[52] U.S. Cl. .................. 252/415; 208/124; 585/487
[58] Field of Search ............ 252/415, 419; 585/487, 585/486

[56] References Cited

U.S. PATENT DOCUMENTS

| 3,673,109 | 6/1972 | Georgescv et al. | 252/415 |
| 4,133,743 | 1/1979 | Boret et al. | 252/415 |
| 4,148,749 | 4/1979 | Ab der Halden et al. | 252/415 |
| 4,199,437 | 4/1980 | Courty et al. | 585/487 |

Primary Examiner—P. E. Konopka
Attorney, Agent, or Firm—Millen & White

[57] ABSTRACT

A catalyst for the steam dealkylation of aromatic hydrocarbons, comprising a carrier and 3 metals, is regenerated in the reaction zone containing the catalyst bed, after disconnection of said zone from the producing unit, by proceeding to the successive steps of: scavenging said zone with hydrogen and then with an inert gas, progressively replacing said inert gas by a gas containing molecular oxygen, burning the catalyst at a temperature lower than 650° C. so as to calcine the carbon deposits of the catalyst, passing through the catalyst bed an air stream containing halogen to increase the halogen content of the catalyst, calcining by means of an air stream at a temperature of 300°–600° C. and purging with an inert gas before reconnecting said reaction zone to the producing unit.

16 Claims, 1 Drawing Figure

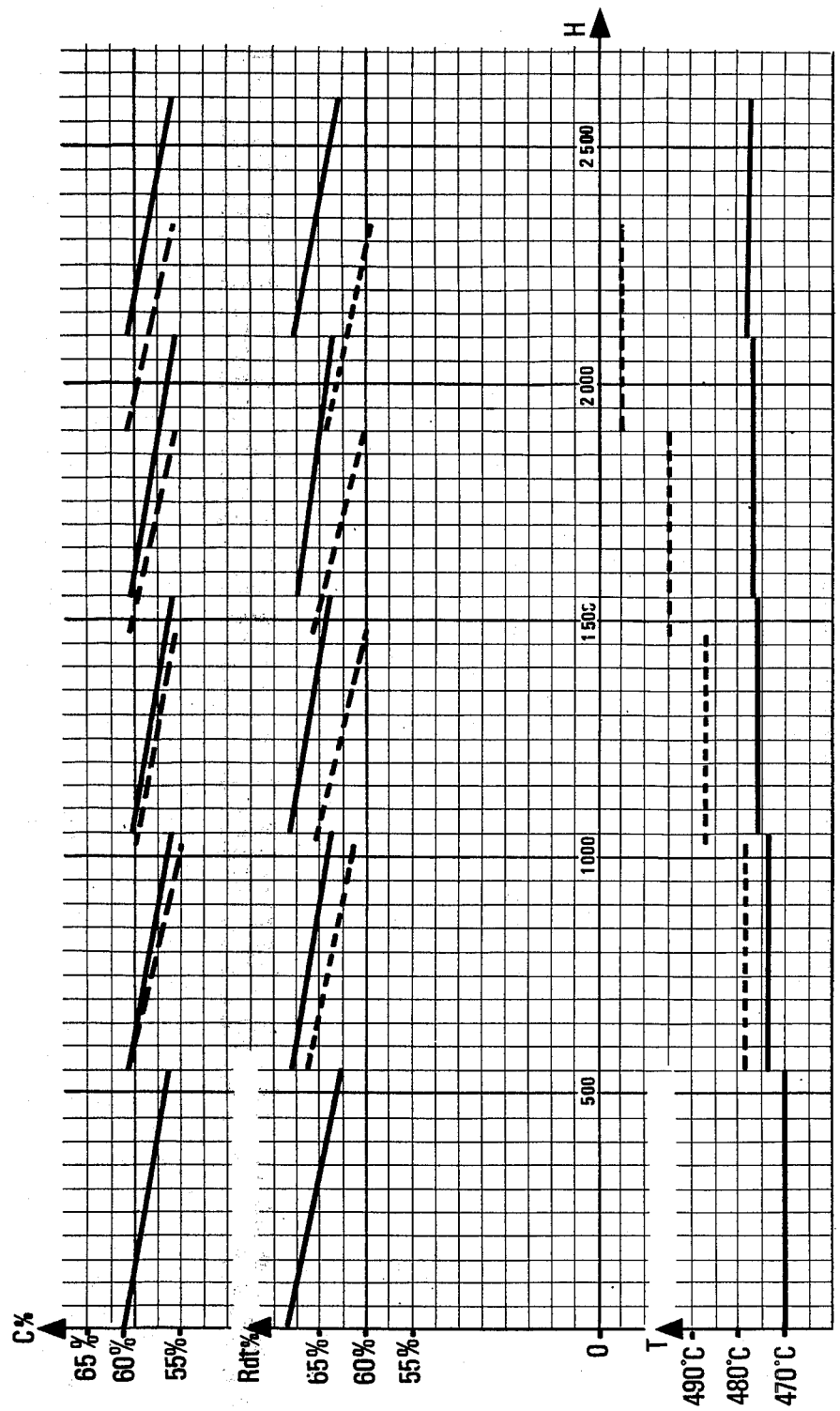

REGENERATION OF A CATALYST FOR AROMATIC HYDROCARBONS STEAM DEALKYLATION

BACKGROUND OF THE INVENTION

The invention concerns steam dealkylation reactions for manufacturing benzene or its lower homologs by dealkylation of toluene or other alkylbenzene hydrocarbons by means of a catalyst containing a carrier, for example, an alumina carrier, and one or more noble metals of the platinum family associated, on the one hand, to at least one other metal or derivative, said metal being selected from rhenium, gold, silver, copper, titanium and, on the other hand, to at least one alkali metal selected from lithium, sodium, potassium, rubidium and cesium. These catalysts further contain halogen as specified below; the invention has particularly for object a process for regenerating the used catalyst.

In the technical literature, many publications indicate that catalysts may be regenerated, particularly those containing one or more metals of the platinum family, by mere combustion of the carbonaceous deposits contained therein; however, said disclosed processes are not finally profitable on an industrial scale, since it has been observed that such a regeneration system does not restore the initial activity of the catalyst and that, after each regeneration, the activity of the catalyst decreases more and more rapidly. In addition, it has also been observed that the selectivity of the so-regenerated catalysts decreases also very rapidly after a relatively short period of operation.

It is an object of the present invention to provide an improved method for regenerating a catalyst used in catalytic steam dealkylation to produce benzene, toluene, xylenes, ethylbenzenes and substantial amounts of hydrogen. The dealkylation may also be performed, for example, to dealkylate toluene, xylenes, ethylbenzene, propylbenzene, methylbenzene or hydrocarbons with condensed rings such as naphthalene, phenanthrene, anthracene etc..., or to dealkylate mesitylene, pseudo cumene, hemimellitene; it is also possible to subject to an aromatization followed with a dealkylation such hydrocarbons as alkylcyclohexane, alkyltetralin, alkyldecalin and alkyldihydroanthracene. Nitrogen containing aromatic compounds, such for example as pyridine derivatives, may also be dealkylated, the nitrogen being eliminated as $NH_3$ or $N_2$.

The steam dealkylation is generally performed in the presence of catalysts, between 300° and 600° C., preferably between 350° and 550° C., under a pressure from 1 to 20 atmospheres and preferably from 3 to 10 atmospheres, with a LHSV ("Liquid Hourly Space Velocity") i.e. liquid VVH (space velocity) from 0.1 to 10 volumes of hydrocarbons per catalyst volume and per hour, preferably from 1 to 5, with a ratio (by moles) $H_2O$/hydrocarbons from 1 to 20, preferably from 3 to 15.

These operating conditions are particularly efficient for dealkylating alkyl aromatic hydrocarbons obtained in the reactions of catalytic reforming or for producing aromatic hydrocarbons ("Aromizing").

The process of this invention for catalyst regeneration thus concerns the process for regenerating and restoring a specific catalyst, so that the reaction system may be operated in a continuous manner over a time period much longer than according to the prior art and without substantial decrease of the activity and the selectivity of the catalyst, the latter substantially recovering, after each regeneration and rejuvenation period, its initial activity and also its initial selectivity.

The regeneration process is particularly applicable to the regeneration of very specific catalysts used for obtaining dealkylated aromatics with high yields (for example high benzene yields) simultaneously with a low rate of degradation of the aromatic ring and giving a reaction gas of high hydrogen content (from about 50 to about 70% by volume of hydrogen) of substantial value.

These specific catalysts contain a carrier, preferably alumina, and from 0.1 to 1%, preferably 0.2 to 0.8% and more particularly 0.25 to 0.65%, by weight with respect to the catalyst, of at least one noble metal of the platinum family, particularly rhodium. They contain 0.5 to 4% and preferably 0.8 to 2% by weight, with respect to the catalyst, of halogen (preferably chlorine).

They also contain either 0.05 to 1%, preferably 0.06 to 0.5% and more preferably, 0.07 to 0.3% of titanium oxide, of formula $TiO_2$, expressed by weight with respect to the catalyst, or 0.05 to 2% of rhenium or of another metal selected from gold, silver and copper.

These catalysts further contain 0.01 to 5% by weight, with respect to the catalyst, of at least one alkali metal selected from lithium, sodium, potassium, rubidium and cesium and optionally 0.01 to 6% by weight, with respect to the catalyst, of at least one additional metal or compound of an additional metal selected from indium, zirconium, thorium, germanium, tin, vanadium, niobium, tantalum, chromium, molybdenum, tungsten, manganese, iron, cobalt and nickel.

Catalysts of a preferred type contain, for example:
(a) an alumina carrier of specific surface higher than 50 $m^2$ per gram and, preferably, higher than 80 $m^2$ per gram, and, by weight:
(b) from 0.1 to 0.5% of rhodium and 0.1 to 0.5% of at least one noble metal selected from the group consisting of platinum, palladium and ruthenium,
(c) from 0.1 to 1% of rhenium,
(d) from 0.5 to 5% of at least one alkali metal selected from the group consisting of lithium, sodium, potassium, rubidium and cesium.

The catalyst carrier is preferably selected from etacubic $\eta_C$, gamma-cubic $\gamma_C$, gamma tetragonal $\gamma_T$, chi cubic $\alpha_C$, kappaorthorhombic K, theta monoclinic $\theta$, delta orthorhombic $\delta$ and rho amorphous $\rho$ aluminas.

Preferably, before any contact with the alkylaromatic hydrocarbons to be dealkylated, the catalyst is subjected to a preliminary reduction treatment by passage of a hydrogen stream at a temperature from 100° to 500° C.

The regeneration process of the invention requires, for the dealkylation reaction, the use of at least two reactors containing the catalyst, one of these reactors being in operation and the second being subsequently disconnected from the circuit and submitted to the regeneration step. Once the regeneration is terminated, the second reactor is put in service while at least one of the ther reactors, if necessary, is in turn disconnected from the circuit to proceed to the regeneration of the catalyst contained therein and so on, so that the dealkylation reaction can be effected in a continuous manner. The reactors in operation are connected in parallel or in series according to the needs.

Various furnaces are arranged at adequate locations to preheat the charge and the intermediary effluents before introducing them into the operating reactors.

For example in the case of two operating reactors, arranged in series, a furnace is provided at the inlet of the first reactor, a second furance being located between the first and the second reactors, etc . . . Simultaneously in a third reactor, there is carried out the regeneration and the rejuvenation of the catalyst contained therein.

There can be designed a system of three reactors wherein the two first reactors, operated in series, may be operated over a very long period of about 300 hours or more and, according to the nature of the charge, the one or the other of these two reactors will be, at a convenient time, disconnected while the third reactor will be put in service and take the place, in the path of the charge, of that one of the two reactors which has been disconnected.

The invention concerns a process for regenerating the dealkylation catalyst and more particularly it concerns a pretreatment of the catalyst before the regeneration treatment itself of this catalyst. The pretreatment as well as the treatment of the deactivated catalyst are performed in the reaction zone which has been disconnected, precisely to proceed to the regeneration of the catalyst contained therein. The regeneration process thus comprises seven steps (a) to (g).

Thus, before the regeneration step itself, the catalyst is first subjected to a hydrogen treatment (step a). This treatment consists of an "elution" or "washing" or "scavenging" of the catalyst with hydrogen. This treatment is performed by passing a hydrogen stream through a bed of the deactivated catalyst. To perform this "washing" the temperature of the catalyst or of the disconnected reaction zone, is maintained between about 300° and 700° C., the pressure in the reaction zone (i.e. in this case the disconnected reaction zone containing the catalyst to be regenerated) being from about 1 to 25 bars, the space velocity being from about 1 to 10,000 $h^{-1}$ (volumes/catalyst volume per hour) and preferably from about 10 to 5,000 $h^{-1}$. Preferably, during the washing with hydrogen, the temperature is progressively decreased from the temperature level of the catalyst bed when the catalytic reaction was discontinued, down to 300° C. Optionally, according to a preferred method, the "elution" or "washing" of the catalyst is performed by means of a hydrogen stream containing halogen or a halogenated compound selected from chlorine, bromine, fluorine and derivatives of said halogens. Preferably, chlorine or a chlorinated compound is used; in the operating conditions at which is performed the hydrogen treatment, the halogen (or the halogen compound optionally present in the hydrogen stream) either is maintained in the form of $Cl_2$ or $Br_2$, or is converted to a hydrogen halide (HCl, HBr, HF) and thus, either in the form of $Cl_2$ or $Br_2$ or as halogenated acid, is fixed on the catalyst so as to compensate the halogen loss of the catalyst occuring during the dealkylation reaction. The amount of halogen or halogenated compound used in the hydrogen stream is so selected that after "elution" or "washing" with hydrogen, the catalyst contains by weight 0.5 to 4% and preferably 0.8 to 2% of halogen with respect to the catalyst. Thus, the content of halogen or halogenated compound in the hydrogen stream is (expressed as halogen) comprised between 0.001 and 10 moles of halogen per 100 moles of hydrogen and preferably from about 0.05 to 2 moles of halogen per 100 moles of hydrogen.

After termination of this pretreatment, the catalyst is subjected to a scavenging with an inert stream (nitrogen for example) to remove residual hydrogen from the disconnected reaction zone containing the catalyst to be regenerated (step b).

Then the catalyst is subjected to the regeneration treatment itself. This treatment, preferably, is conducted as follows:

first, in a first step, the inert gas used to scavenge the pretreated catalyst as above mentioned, is progressively replaced with a gas containing molecular oxygen (step c); the oxygen partial pressure is at least 0.005 bar and, preferably, from about 0.02 to 0.14 bar, the temperature of the gas at the inlet of the disconnected reaction zone being comprised between about 300° and 550° C. and preferably between about 350° and 450° C.

Then in step (d), the gas containing molecular oxygen is passed over the catalyst, said gas being introduced at a temperature from 300° to 550° C. under a pressure of from about 1 to 25 bars so as to remove the coke deposited on the catalyst. The space velocity is from 1 to 500 volumes/catalyst volume per hour. The gas used to produce the combustion of the coke may optionally contain 0.01 to 10% by volume of steam. It may optionally contain a halogen or a halogen comound, in a sufficient amount (for example from 0.01 to 10 moles of halogen and preferably from 0.05 to 2 moles) to avoid a too substantial loss of the halogen contained in the catalyst. The gas used may optionally contain simultaneously steam and a halogen or a halogen compound.

The formation of a combustion front (or ignition zone) which slowly passes through the catalyst bed is observed, during the treatment of the catalyst by means of the molecular oxygen containing gas. The oxygen content of the gas is so regulated as to prevent the temperature of said combustion front from exceeding about 650° C. Thus, this front is maintained preferably at a temperature which does not exceed by more than about 150° C. the temperature of the gas at the inlet of the catalyst bed. As the combustion front progresses through the catalyst bed, the inlet side of the reactor containing said catalyst bed cools down, but, on the contrary, on the outlet side of the catalyst bed, the temperature progressively increases as a result of the heat evolution produced by the combustion of the carbonaceous materials on the catalyst. When this exothermic effect is no longer observed, the calcination in pure air (or an equivalent gas) may be continued at a temperature from about 300° to 500° C. for a sufficient time, so as to reduce the carbon content of the catalyst by at least 90% of its initial content before regeneration, i.e. at the time of the disconnection of the reaction zone containing the used catalyst.

Then, the combustion of the carbonaceous material being complete, the catalyst is reactivated (step e), by maintaining it in a stream of air or an equivalent gas (space velocity from about 1 to 10,000 and preferably 100 to 5,000 volumes/catalyst volume per hour at a temperature from about 300° to 500° C., preferably in the presence of at least one halogen or halogenated compound in a sufficient amount to proceed to an optimum reactivation of the active species, i.e. in a sufficient amount to bring the halogen content of the catalyst to its optimum value once the reactivation is terminated. This air-halogen or air-halogen compound mixture may optionally contain 0.01 to 10% by volume of steam. The pressure in the catalyst zone during this operation is maintained between about 1 and 25 bars. The catalyst is maintained in contact with the halogen or halogen derivative containing gas for a sufficient time, so that the catalyst, ready for use, contains 0.5 to 4% by weight, preferably 0.8 to 2% by weight of halogen with respect to the dry catalyst mass. The preferred halogen is chlorine. In order to adjust the halogen content of the catalyst, the halogen may be used simply in its elemental form, but in order to facilitate the handling, it is preferred to use halogen derivatives (preferably chlorine derivatives) which are normally in the liquid state, provided however that these compounds may release their halogen when they are in contact with the catalyst, under the indicated operating conditions.

The preferred chlorinated derivatives which can be normally used are chlorinated hydrocarbons having from 1 to 4 carbon atoms per molecule, for example carbon tetrachloride, chloro-ethylene, dichloroethylene, tert. butyl chloride, etc . . .

Generally, in order to avoid any corrosion, it is preferred to discontinue the halogen treatment as soon as it is observed that the halogen content of the gas issued from the regeneration zone is close to the halogen content of the gas supplied to said regeneration zone.

Then, after this halogenation phase, the catalyst is subjected to a calcination step (step f), in the presence of air or of an equivalent gas, at a temperature from about 300° to 600° C., preferably from 400° to 500° C. The air flow rate is such that the space velocity is from 1 to 10,000, and preferably from 100 to 5,000 volumes/catalyst volume per hour. The pressure is comprised between about the atmospheric pressure and 25 bars. The duration of the calcination step is from about 15 minutes to 180 minutes.

Finally, after said calcination, the reactor and the catalyst contained therein are purged (step g), by passing a stream of inert gas, for example nitrogen or another gas, so as to remove any oxygen trace.

Said purge may be performed, for example, under the same operating conditions as those used in the preceding calcination step.

Optionally, after said purge with an inert gas, the catalyst is advantageously reduced by means of a hydrogen containing gas and for example by means of a gas produced by the unit itself, before connecting again the reactor containing the regenerated and reactivated catalyst to the dealkylation unit.

This reduction is thus conducted in the presence of a gas containing at least 10% (by mole) of hydrogen, preferably as dry gas, i.e. containing less than 0.5% by weight of water; the reduction temperature is comprised between about 200° and 700° C. and preferably between about 325° and 550° C.; the total pressure in the reactor is comprised between the atmospheric pressure and about 25 bars. The space velocity of hydrogen is from about 1 to 10,000 volumes of hydrogen per catalyst volume and per hour and preferably from 10 to 5,000. The reduction time is preferably not shorter than 1 hour without exceeding about 30 hours.

The process of the invention thus provides during the regeneration of the catalyst, for a clear improvement of the activity and selectivity as compared to the conventional regeneration methods which do not include the initial washing or elution with a hydrogen stream.

EXAMPLE

This example concerns the use of a dealkylation catalyst prepared as follows: a $\gamma_C$ alumina carrier of the trade, consisting of balls of a diameter from 1.6 to 2.5 mm, having a specific surface of 210 m²/g and a pore volume of 63 ml per 100 g, previously stoved at 70° C. in a steam-saturated atmosphere, is impregnated as follows:

1,000 g of dry carrier, stoved at 70° C., are contacted with 1,500 ml of a solution containing 5.1 g of rhodium in the form of rhodium trichloride hydrate and 40 ml of pure hydrochloric acid of a grade convenient for analysis (d=1.19). After exhaustion of the solution, it is observed that rhodium is distributed homogeneously in the carrier balls. The impregnated carrier, after draining at 100° C. for 1 hour and then at 200° C. for 2 hours, is calcined at 350° C. for 1 hour. The catalyst is then contacted with 1,400 ml of a solution containing 9.4 g of ammonium perrhenate and 20 ml of hydrochloric acid. After exhaustion of said solution, the catalyst is dried, after draining at 100° C. for 1 hour and then at 200° C. for 2 hours, and then calcined at 290° C. for 5 hours in the presence of air.

The catalyst is then impregnated in a dry state with 560 ml of a solution containing 10.2 g of potassium, as nitrate, dried at 100° C. for one hour, then at 200° C. for 5 hours and directly reduced with dry hydrogen at 300° C. for 30 minutes and then at 520° C. for one hour.

The resulting catalyst had the following composition by weight:
0.5% of rhodium
0.6% of rhenium
1.0% of potassium
0.85% of chlorine.

The obtained catalyst is subjected to a long duration test of toluene dealkylation in a system with 3 fixed bed reactors, traversed in series by the charge.

The operating conditions are as follows:
charge:
    toluene: 98.3% by weight;
    xylenes: 1.7% by weight
space velocity (L.H.S.V.): 2 volumes of charge per volume of catalyst and per hour.
    ratio H₂O/hydrocarbon=6 moles/mole
pressure: 7 bars.

The temperature is so adjusted that, at the beginning of each cycle, after regeneration and reactivation, the same conversion rate of toluene is obtained; thus the starting temperature of the first cycle i.e. with the fresh catalyst, is 470° C.

At the beginning of the cycle the following results are obtained:
    molar conversion of toluene: 61%
    molar selectivity to benzene: 95.8%
    molar yield of benzene: 58.4%

After 550 hours of run, a regular fall of the toluene conversion rate and of the benzene yield is observed: the molar conversion of toluene is 56% and the benzene yield is 53%. It is then decided to regenerate the catalyst in the third reactor through which passes the charge which is, accordingly, disconnected from the circuit, so as to proceed to said regeneration in the reactor itself. For this regeneration, a first experiment is conducted, in conformity with the method of the present invention:

the charge and steam supply to the third reactor is discontinued, then the catalyst of said third reactor is washed with hydrogen for 4 hours (step a of the process) while progressively decreasing the temperature of the catalyst bed from the temperature of the end of the cycle, i.e. about 480° C., prevailing at the beginning of the hydrogen washing, to a temperature not below 300° C. (pressure: 1 bar).

The hydrogen used contains 0.02 mole of chlorine per 100 moles of hydrogen. After this washing with hydrogen, said hydrogen is purged by a scavenging with nitrogen for 2 hours (step b of the process).

Then, the temperature of the catalyst bed being 300° C., there is introduced, at 400° C., an inert gas containing oxygen at a partial pressure of 0.015 bar (step c of the process). Then, in step d of the process, the temperature is maintained at about 400° C. for the time required for removing 95% of the coke deposits (pressure: 1 bar). The temperature of the combustion front was not in excess of 550° C. The gas used for this combustion had a chlorine content of 0.02% by mole; the gas further contains 0.03% by volume of steam.

Once the combustion is terminated, the catalyst is treated (step e of the process) with air and simultaneously with chloroethylene whose chlorine concentration, by mole, is 0.02% with respect to the air; the air also contains 0.02% by volume of water. This treatment with air is performed at a temperature of 450° C. for 2 hours, the space velocity of air being 500 volumes per volume of catalyst and per hour, then the catalyst is calcined in air at the same temperature for two further hours (step f of the process); pressure 1 bar; air flow rate: 500 volumes per volume of catalyst and per hour.

Before proceeding to the reconnection of the reaction zone containing the catalyst which has just been regenerated, for a new cycle, the catalyst is purged with nitrogen (step g of the process) and is then subjected to a reduction in the presence of hydrogen, at a temperature of 450° C. for 2 hours.

In the case of the comparative example (ordinary regeneration) the catalyst is not subjected to hydrogen washing, all the other operations being unchanged.

The results obtained for 5 cycles are shown diagrammatically in the drawing, where there is shown simultaneously the evolution, versus time in hours "H", of the molar conversion of toluene "C" and of the benzene molar yield "Rdt", during the first cycle with fresh catalyst and then during each of the four following cycles conducted after four successive regenerations performed at the end of the 4 first cycles. The diagram also shows the evolution of the temperature T of the catalyst bed in relation with the cycles. As a matter of fact, this temperature varies since the catalyst loses a part of its activity and selectivity during time, said loss being not completely compensated after each regeneration: accordingly it is necessary to increase the reaction temperature in order to compensate for these decreases of activity and selectivity.

The drawing also shows, by way of comparison, the results obtained in a dealkylation test conducted under the same conditions as above described with successive regenerations of the considered catalyst bed. The regeneration, in this comparative test, is conducted as above indicated. However, the catalyst to be regenerated is subjected neither to the preliminary treatment with hydrogen nor to the nitrogen purge following this preliminary treatment.

The regeneration thus directly begins, after a scavenging for one hour with an inert gas, by the introduction of the same gas, at 300° C., containing oxygen under a partial pressure of 0.015 bar.

In the drawing, the results obtained by the regeneration according to the invention, are shown in solid lines and the results obtained without regeneration according to the invention, are shown in dashed lines.

The following observations can be made:

For the first cycle, obviously, the results are identical, but, thereafter, as soon as the first regeneration takes place, advantages are observed in using the regeneration method according to the invention as compared to a method not in conformity with the invention, said advantages consisting of a decrease of the activity loss during the first cycle and then from one cycle to the next and, on the other hand, of a still more significant decrease of the drop in the benzene yield, i.e. the selectivity.

In addition, a regeneration conforming with the invention provides for an increase of the duration of each cycle as compared to the duration of the cycles when not regenerating according to the invention.

Moreover, the temperature increase at the beginning of each cycle, after regeneration, which is necessary to compensate for the loss of activity of the catalyst, is much less substantial when regenerating according to the invention than when regenerating without conforming to the invention.

What is claimed is:

1. In a continuous process for steam dealkylation of aromatic hydrocarbons in the presence of a catalyst comprising a carrier and, by weight, from 0.1 to 1% of at least one noble metal of the platinum family, from 0.5 to 4% of halogen, a second metal or metal compound wherein the metal is selected from titanium, rhenium, copper, silver and gold, and a third metal or metal compound wherein the metal is selected from lithium, sodium, potassium, rubidium and cesium, the improvement wherein said process is effected in at least two reaction zones, each of said zones being alternatively disconnected for regeneration of the catalyst contained therein and then reconnected to the reaction system; wherein said regeneration is effected by a process comprising the steps of:
(a) passing through the disconnected reaction zone and the catalyst contained therein a hydrogen stream at a space velocity of from 1 to 10,000 volumes per volume of catalyst per hour, a pressure of from about 1 to 25 bars and a temperature of from about 300° to 700° C.;
(b) scavenging the hydrogen-washed catalyst with an inert gas stream to remove any residual hydrogen;
(c) progressively replacing the inert gas with a gas containing molecular oxygen;
(d) burning off coke deposited on the catalyst contained in the disconnected reaction zone by passing therethrough a gas containing molecular oxygen at an oxygen partial pressure of at least 0.005 bar and further containing from 0.01 to 10% by volume of steam, said gas being introduced into the disconnected reaction zone at a temperature between about 300° and 550° C., a pressure of from about 1 to 25 bars and a space velocity of from 1 to 500 volume per catalyst volume per hour, the oxygen content of the gas being so adjusted as to limit the temperature of the combustion front passing through the catalyst to a maximum of 650° C., the difference between the temperature of said front and the temperature of the gas supplied at the inlet of the catalyst bed being not greater than 150° C., calcination being continued, after the combustion front has passed through the catalyst bed, at a temperature of from about 300°-500° C. for a time sufficient to reduce the initial carbon content of the catalyst at the time of disconnecting the reaction zone by at least 90%;

(e) reactivating the catalyst by passing therethrough a stream of air or an equivalent gas containing at least one halogen or halogenated compound, at a space velocity of from about 1 to 10,000 volumes per volume of catalyst per hour, a temperature of from about 300° to 500° C., and a pressure of from about 1 to 25 bars, for a time sufficient to bring the halogen content of the catalyst to a value between 0.5 and 4% by weight;

(f) calcining the reactivated catalyst by passing therethrough a stream of air or an equivalent gas, at a temperature of from about 300° to 600° C. a space velocity of from about 1 to 10,000 volumes per volume of catalyst per hour and a pressure of from about 1 to 25 bars; and (g) purging the disconnected reaction zone by passing therethrough an inert gas stream.

2. A process according to claim 1, wherein the catalyst carrier is alumina and wherein the catalyst contains at least rhodium.

3. A process according to claim 1, wherein, during step (a), the space velocity of hydrogen is from about 10 to 5,000 volumes per catalyst volume per hour.

4. A process according to claim 1, wherein, during step (a), the hydrogen stream contains a halogen or a halogen compound in an amount such that, at the end of step (a), the catalyst contains, by weight, about 0.5 to 4% of halogen.

5. A process according to claim 4, wherein, at the end of step (a), the catalyst contains, by weight, 0.8 to 2% of halogen.

6. A process according to claim 4, wherein the halogen is chlorine.

7. A process according to claim 4, wherein the halogenated compound is a chlorine compound.

8. A process according to claim 1, wherein, during step (d), the gas used for the combustion contains a halogen or a halogen compound.

9. A process according to claim 1, wherein, after the purge of step (g), the catalyst, before being reused as dealkylation catalyst, is subjected to reduction by means of a hydrogen containing gas.

10. A process according to claim 1, wherein in step (c), the oxygen partial pressure is from about 0.02 to 0.14 bar.

11. A process according to claim 8, wherein the amount of said halogen or halogen compound is from 0.001 to 10 moles of halogen.

12. A process according to claim 1, wherein in step (e), the space velocity of air or equivalent gas is from 100 to 500 volumes per catalyst volume per hour.

13. A process according to claim 1, wherein in step (e), the air or equivalent gas contans from 0.01 to 10% by volume of steam.

14. A process according to claim 1, wherein in step (f), the space velocity of the air or equivalent gas is from 100 to 5,000 volumes per catalyst volume per hour.

15. A process according to claim 9, wherein the reduction is effected by a gas containing at least 10 mol % of hydrogen and less than 0.5 weight % of water, at a temperature of from about 200° to 700° C., a pressure of from about atmospheric pressure to about 25 bars and a space velocity of from about 1 to 10,000 volumes per catalyst volume per hour.

16. A process according to claim 15, wherein the temperature of reduction is from 325° to 550° C. and the space velocity is from 10 to 5,000 volumes per catalyst volume per hour.

* * * * *